United States Patent [19]

Ishizumi et al.

[11] Patent Number: 4,540,695

[45] Date of Patent: Sep. 10, 1985

[54] AMINONAPHTHACENE DERIVATIVES AND THEIR USE

[75] Inventors: Kikuo Ishizumi, Toyonaka; Naohito Ohashi, Nishinomiya; Michihisa Muramatsu, Osaka, all of Japan

[73] Assignee: Sumitomo Chemical Co., Ltd., Osaka, Japan

[21] Appl. No.: 407,278

[22] Filed: Aug. 11, 1982

[30] Foreign Application Priority Data

Aug. 12, 1981 [JP] Japan .................................. 56-127227
May 10, 1982 [JP] Japan .................................. 57-78708

[51] Int. Cl.³ ........................ A61K 31/13; C07C 97/07
[52] U.S. Cl. ...................................... 514/239; 260/365; 514/467; 514/533; 514/534; 514/546; 514/548; 514/550; 514/617; 514/628; 514/630; 514/656; 544/89; 549/451; 549/452
[58] Field of Search ........................... 260/365; 544/89; 549/341, 342, 451, 452; 424/248.55, 248.58, 278, 305, 309, 324, 330

[56] References Cited

U.S. PATENT DOCUMENTS

| | | | |
|---|---|---|---|
| 1,922,480 | 8/1933 | Koehler | 260/59 |
| 4,104,306 | 8/1978 | Bernstein et al. | 424/325 X |
| 4,107,423 | 8/1978 | Arcamone et al. | 260/365 X |
| 4,302,398 | 11/1981 | Hassall et al. | 260/365 |

OTHER PUBLICATIONS

Arcamone, "Doxorubicin—Anticancer Antibiotics", (Medicinal Chemistry—a Series of Monographs; published by Academic Press, New York), 1981, (Table of Contents and pp. 163-193 and 259-299).

*Primary Examiner*—Richard Raymond

*Attorney, Agent, or Firm*—Birch, Stewart, Kolasch & Birch

[57] ABSTRACT

Aminonaphthacene derivatives of the formula:

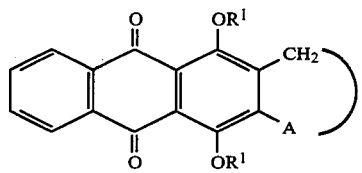

wherein A is either one of the following groups:

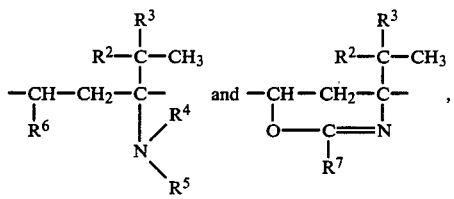

wherein $R^1$ is a hydrogen atom or a group of the formula: $-COR^7$, $R^2$ and $R^3$ are each a lower alkoxy group or, when taken together, represent an ethylenedioxy group or an oxo group, $R^4$ and $R^5$ are both hydrogen atoms or either one of them is a hydrogen atom and the other is a group of the formula: $-COR^7$, $R^6$ is a hydrogen atom, a hydroxyl group or a group of the formula: $-OCOR^7$ and $R^7$ is a lower alkyl group, a halo(lower)alkyl group, a phenyl group or a halophenyl group, which are useful as anti-microbial and/or anti-tumor agents, or as intermediates in their production.

7 Claims, No Drawings

AMINONAPHTHACENE DERIVATIVES AND THEIR USE

The present invention relates to aminonaphthacene derivatives and their production.

The aminonaphthacene derivatives are representable by the formula:

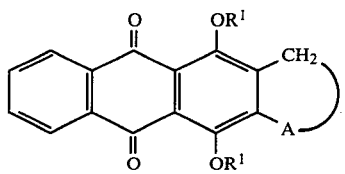

wherein A is either one of the following groups:

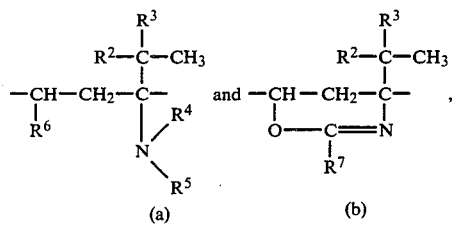

$R^1$ is a hydrogen atom or a group of the formula: —$COR^7$, $R^2$ and $R^3$ are each a lower alkoxy group or, when taken together, represent an ethylenedioxy group or an oxo group, $R^4$ and $R^5$ are both hydrogen atoms or either one of them is a hydrogen atom and the other is a group of the formula: —$COR^7$, $R^6$ is a hydrogen atom, a hydroxyl group or a group of the formula: —$OCOR^7$ and $R^7$ is a lower alkyl group, a halo(lower)alkyl group, a phenyl group or a halophenyl group.

Among them, preferred are those of the formula (I) wherein $R^1$ is hydrogen and, in case of A representing the group (a), $R^6$ is hydroxyl or, in case of A representing the group (b), $R^7$ is methyl or trifluoromethyl. Particularly preferred are compounds wherein $R^1$ is hydrogen, $R^2$ and $R^3$ represent oxo and, in case of A representing the group (a), $R^6$ is hydroxyl or, in case of A representing the group (b), $R^7$ is methyl or trifluoromethyl.

In the foregoing and subsequent descriptions, the term "lower" is intended to mean any group having not more than 8 carbon atoms, preferably not more than 5 carbon atoms, more preferably not more than 3 carbon atoms. The term "halogen" means fluorine, chlorine and bromine, inclusively. Thus, examples of lower alkyl are methyl, ethyl, n-propyl, isopropyl, etc. Examples of lower alkoxy are methoxy, ethoxy, n-propoxy, isopropoxy, etc. Examples of halo(lower)alkyl are chloromethyl, dichloromethyl, 2-chloroethyl, 3-chloropropyl, trifluoromethyl, 2-bromoethyl, etc. Examples of halobenzoyl are o-chlorobenzoyl, m-chlorobenzoyl, p-chlorobenzoyl, o-bromobenzoyl, p-fluorobenzoyl, 2,4-dichlorobenzoyl, 3,5-dichlorobenzoyl, etc.

The aminonaphthacene derivatives of the formula (I) cover the following two groups of compounds:

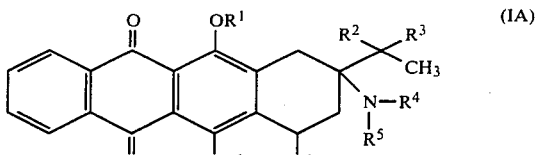

and

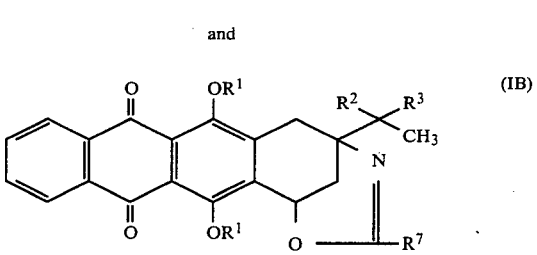

wherein $R^1$, $R^2$, $R^3$, $R^4$, $R^5$, $R^6$ and $R^7$ are each as defined above.

Further, the aminonaphthacene derivatives (I) can include various steric and optical isomers, since they have two asymmetric atoms, i.e. at the 7- and 9-positions, except the case wherein $R^6$ is hydrogen. Among those isomers, preferred are the compounds wherein the C—O bond at the 7-position and the C—N bond at the 9-position take a cis-configuration. Also preferred are the optical isomers wherein the steric configuration at the 9-position is the same as that at the 2-position of the l-isomer of the starting tetrahydronaphthalene compound of the formula (II) as hereinafter stated.

The aminonaphthacene derivatives (I) have been unexpectedly found to show an anti-microbial activity and an anti-tumor activity. Thus, they are useful as pharmaceuticals for human beings and mammals. They can be administered parenterally, orally or locally to warm-blooded animals and human beings in the form of conventional pharmaceutical preparations. For instance, they can be administered in the form of conventional solid pharmaceutical preparations such as tablets, capsules, powders or granules, or in the form of conventional liquid pharmaceutical preparations such as suspensions, emulsions or solutions. The daily dosage may vary depending upon the administration route and is usually between 0.1 and 300 mg/kg.

The aminonaphthacene derivatives (I) can be produced from the corresponding tetrahydronaphthalene compound of the formula:

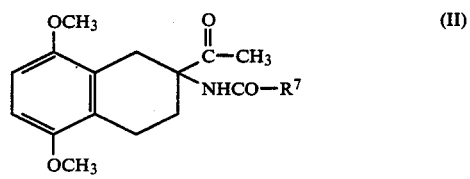

wherein $R^7$ is as defined above according to the following Scheme A:

Scheme A

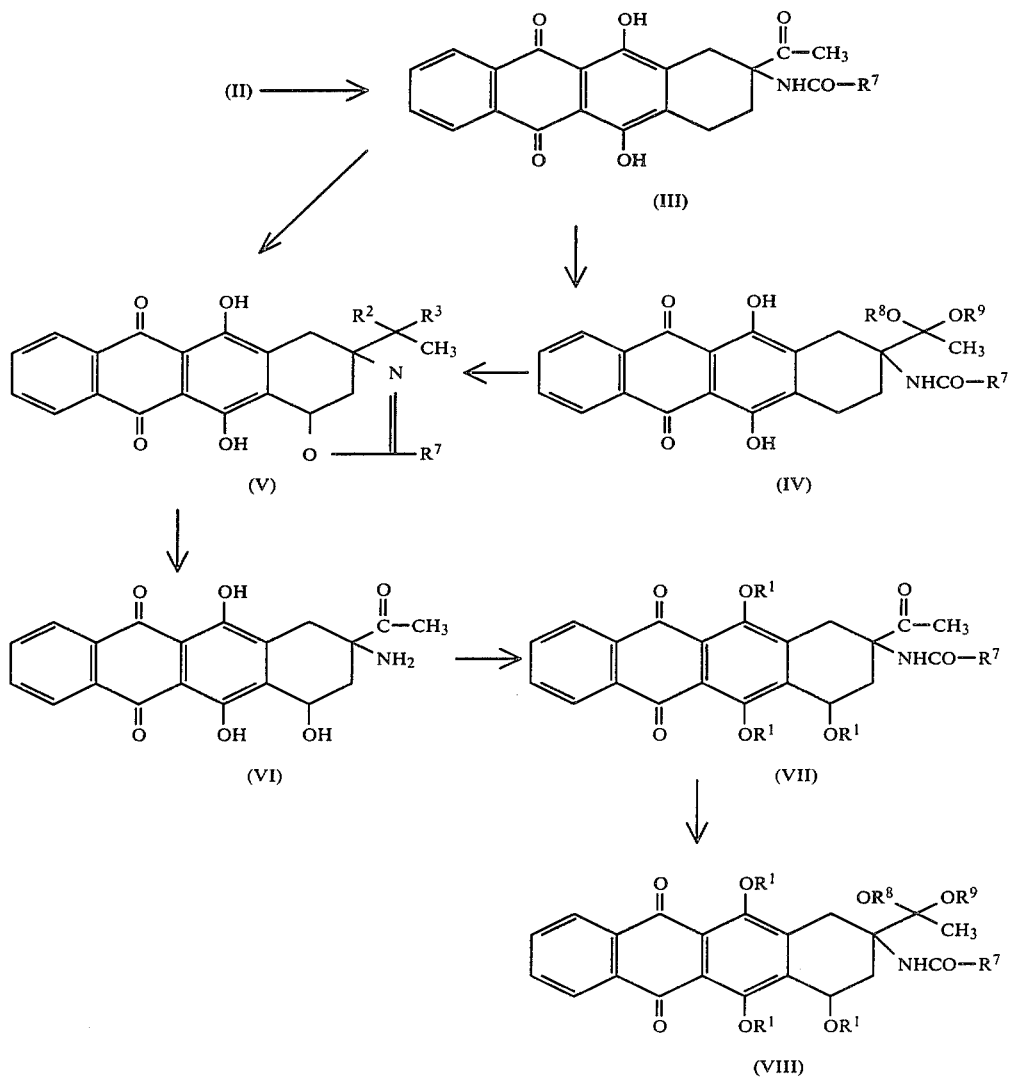

wherein $R^1$, $R^2$, $R^3$, $R^4$, $R^5$, $R^6$ and $R^7$ are each as defined above and $R^8$ and $R^9$ are each lower alkyl or, when taken together, represent ethylene.

Namely, the tetrahydronaphthalene compound (II) is reacted with phthalic anhydride in the presence of a Lewis acid to give the acetyl compound (III). As the Lewis acid, there may be used aluminum chloride, aluminum bromide, ferric chloride, stannic chloride, etc., among which aluminum chloride is the most preferred in ready availability and easy handling. The reaction may be carried out under the conditions as conventionally adopted for the Friedel-Crafts reaction and preferably while melting in the presence of a salt (e.g. sodium chloride) in the absence of any solvent.

The thus prepared acetyl compound (III) is subjected to acetalation to give the corresponding acetal compound (IV). The acetalation may be effected by a per se conventional procedure.

The acetyl compound (III) or the acetal compound (IV) may be reacted with a halogenating agent in an inert solvent to give the dihydrooxazine compound (V). Examples of the halogenating agent are bromine, chlorine, N-bromosuccinimide, N-chlorosuccinimide, etc. As the inert solvent, there may be employed a halogenated hydrocarbon (e.g. carbon tetrachloride, chloroform, dichloroethane, tetrachloroethane), an ether (e.g. tetrahydrofuran, dioxane), an aliphatic hydrocarbon (e.g. hexane, cyclohexane, heptane), a ketone (e.g. acetone, methylethylketone), benzene, acetic acid, water, etc. These inert solvents may be used alone or in combination. The reaction can proceed at room temperature, but heating up to the boiling point of the inert solvent may be effected for acceleration of the reaction. When desired, the incorporation of a radical initiator (e.g. N,N'-azobisisobutyronitrile, benzoyl peroxide) into the reaction system or the irradiation of the reaction mixture with visible rays may be effected for promotion of the reaction.

Hydrolysis of the dihydrooxazine compound (V) in the presence of an acidic substance such as a mineral acid (e.g. hydrochloric acid, sulfuric acid) or an organic sulfonic acid (e.g. p-toluenesulfonic acid) in an aqueous medium affords the amino compound (VI). The aqueous medium may comprise water alone or a mixture of water and one or more organic solvents chosen from alcohols (e.g. methanol, ethanol, isopropanol), ethers (e.g. tetrahydrofuran, dioxane), ketones (e.g. acetone, methylethylketone), halogenated hydrocarbons (e.g. chloroform, dichloroethane), acetic acid and the like. The reaction can proceed at room temperature, but heating up to the boiling point of the solvent is favorable for promotion of the reaction.

The amino compound (VI) can be acylated by reacting with an acid of the formula: $R^7$—COOH wherein $R^7$ is as defined above or its reactive derivative at the carboxyl group to give the corresponding acylamino compound (VII). As the reactive derivative of the acid, there may be exemplified acid halides, acid anhydrides, etc. When the acid itself is used, the acylation is favorably effected in the presence of a dehydrating agent such as N,N'-dicyclohexylcarbodiimide. When the reactive derivative of the acid is employed, the acylation is normally carried out in the presence of a base such as sodium carbonate, sodium hydrogen carbonate, triethylamine, pyridine, 4-dimethylaminopyridine, lutidine, collidine, etc. Depending upon the amount of the acid or its reactive derivative to be used, there is obtainable the acylamino compound (VII) wherein $R^1$ is hydrogen or —$COR^7$ as the major product. For production of the acylamino compound (VII) wherein $R^1$ is hydrogen as the major product, the acid or its reactive derivative may be used in an amount of 1 to 3 mol to 1 mol of the amino compound (VI). For production of the acylamino compound (VII) wherein $R^1$ is —$COR^7$, the acid or its reactive derivative may be used in an amount of not less than 4 mol to 1 mol of the amino compound (VI). The acylation is usually carried out in an inert solvent such as a halogenated hydrocarbon (e.g. dichloromethane, chloroform, dichloroethane), an ether (e.g. tetrahydrofuran, dioxane), a ketone (e.g. acetone, methylethylketone), dimethylformamide or dimethylsulfoxide. Alternatively, the base in a liquid state may be used as such as the reaction medium. The reaction temperature may be normally from room temperature to the boiling point of the reaction medium.

The acylamino compound (VII) may be subjected to acetalation to give the acetalated compound (VIII). The acetalation may be accomplished by a per se conventional procedure.

The products in the above conversions, i.e. the acetyl compound (III), the acetal compound (IV), the dihydrooxazine compound (V), the amino compound (VI), the acyl compound (VII) and the acetalated compound (VIII), are all covered by the formula (I) and are thus within the objective aminonaphthacene derivatives of the invention.

The tetrahydronaphthalene compound (II) used as the starting material in the above conversions is novel and can be produced according to the following Scheme B:

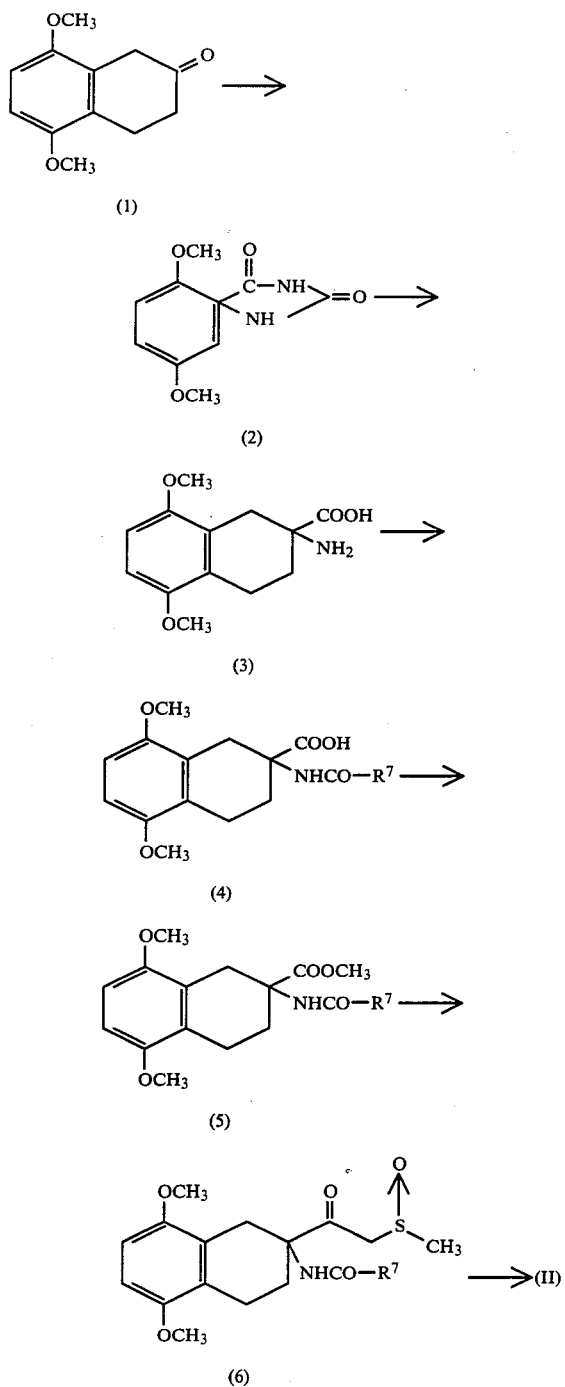

wherein $R^7$ is as defined above.

The conversions as shown in Scheme B may be carried out, for instance, by reacting the compound (1) with ammonium carbonate and potassium cyanide to give the compound (2), hydrolyzing the latter in the presence of barium hydroxide in an aqueous medium to give the compound (3), acylating the latter with an acid chloride or an acid anhydride to give the compound (4), esterifying the latter with methanol in the presence of an acid catalyst such as sulfuric acid to give the compound (5), reacting the latter with methylsulfinyl carbanion prepared from dimethylsulfoxide and sodium hydride to give the compound (6) and desulfurizing the latter with amalgamated aluminum or zinc to give the tetrahydronaphthalene compound (II).

As stated above, the aminonaphthacene derivatives (I) have asymmetric carbon atoms and include many steric isomers. When the starting tetrahydronaphthalene compound (II) is optically active, the products in Scheme A can be also optically active. In order to obtain the tetrahydronaphthalene compound (II) in an optically active form, the compound (4) in Scheme B may be subjected to optical resolution. Using the thus obtained optically active compound (4), the subsequent conversions are effected to give the correspondingly optically active tetrahydronaphthalene compound (II).

In the said resolution of the compound (4) in a racemic state, it may be treated with an optically active amine such as l-ephedrine or l- or d-α-phenethylamine as a resolving agent to give the diastereomer salts of the compound (4), which are separated into the d-form compound (4)/optically active amine salt and the l-form compound (4)/optically active amine salt by utilization of the difference in solubility. Decomposition of each diastereomer salt with a mineral acid affords the corresponding optically active (i.e. d- or l-form) compound (4).

Specific examples of the aminonaphthacene derivatives (I) which cover not only the racemic form but also the optically active form are as follows:
9-Acetyl-9-acetamino-6,11-dihydroxy-7,8,9,10-tetrahydro-5,12-naphthacenedione;
9-Acetamino-9-(1-ethylenedioxy)ethyl-6,11-dihydroxy-7,8,9,10-tetrahydro-5,12-naphthacenedione;
9-Acetyl-6,11-dihydroxy-7,8,9,10-tetrahydro-7,9-(1-oxa-3-aza-2-methyl-2-propeno)naphthacen-5,12-dione;
9-(1-Ethylenedioxy)ethyl-6,11-dihydroxy-7,8,9,10-tetrahydro-7,9-(1-oxa-3-aza-2-methyl-2-propeno)naphthacene-5,12-dione;
9-Amino-9-acetyl-6,7,11-trihydroxy-7,8,9,10-tetrahydro-5,12-naphthacenedione;
9-Acetyl-9-acetamino-6,7,11-trihydroxy-7,8,9,10-tetrahydro-5,12-naphthacenedione;
9-Acetyl-9-benzoylamino-6,7,11-trihydroxy-7,8,9,10-tetrahydro-5,12-naphthacenedione;
9-Acetyl-9-(p-chlorobenzoyl)amino-6,7,11-trihydroxy-7,8,9,10-tetrahydro-5,12-naphthacenedione;
9-Acetyl-9-amino-6,11-dihydroxy-7,8,9,10-tetrahydro-5,12-naphthacenedione;
9-Acetyl-9-trifluoroacetylamino-6,11-dihydroxy-7,8,9,10-tetrahydro-5,12-naphthacenedione;
9-Trifluoroacetamino-9-(1-ethylenedioxy)ethyl-6,11-dihydroxy-7,8,9,10-tetrahydro-5,12-naphthacenedione;
9-Acetyl-9-trifluoroacetamino-6,7,11-trihydroxy-7,8,9,10-tetrahydro-5,12-naphthacenedione;
9-Acetyl-9-acetamino-6,7,11-triacetoxy-7,8,9,10-tetrahydro-5,12-naphthacenedione, etc.

Practical and presently preferred embodiments of the invention are shown in the following Examples. Some embodiments of the procedures for preparation of the starting tetrahydronaphthalene compound (II) are also shown in the following Reference Examples. In those Examples and Reference Examples, there are included not only a racemic form (i.e. dl-form) but also optically active forms (i.e. d- and l-forms).

REFERENCE EXAMPLE 1

(1) To a mixture of 1,4-dimethoxy-6-tetralone (82.4 g), water (1200 ml) and ethanol (1200 ml), ammonium carbonate (345.6 g) and potassium cyanide (34.0 g) were added, and resultant mixture was stirred while refluxing for 1 hour. The reaction mixture was concentrated under reduced pressure, allowed to stand at room temperature overnight and cooled with ice water for 2.5 hours. The precipitated crystals were collected by filtration to give spiro[1,2,3,4-tetrahydro-5,8-dimethoxynaphthalene-2,4'-hydantoin]. M.P., 274°–276° C.

(2) To the hydantoin (102.5 g) as prepared above, water (3000 ml) and barium hydroxide octahydrate (630 g) were added, and the resultant mixture was refluxed in a nitrogen stream for 36 hours. The reaction mixture was cooled to room temperature, admixed with water (1000 ml) and adjusted to pH 0.6 with 6N sulfuric acid at room temperature. The resulting mixture was warmed to a temperature of 40° to 45° C., a celite (300 g) was added thereto, and stirring was continued for 30 minutes, followed by separation of insoluble materials by filtration. The filtrate was adjusted to pH 6.0 with diethylamine and cooled with ice water for 2 hours. The precipitated crystals were collected by filtration to give 2-amino-1,2,3,4-tetrahydro-5,8-dimethoxy-2-naphthoic acid. M.P., 264°–266° C.

(3) To the above obtained aminonaphthoic acid (46.5 g), anhydrous pyridine (900 ml) and acetic anhydride (90 g) were added, and the resulting mixture was stirred at room temperature overnight. After removal of the pyridine under reduced pressure, 3% hydrochloric acid (700 ml) was added thereto, and the resulting mixture was stirred at room temperature for 3 hours. The precipitated crystals were collected by filtration to give 2-acetamino-1,2,3,4-tetrahydro-5,8-dimethoxy-2-naphthoic acid. M.P., 282°–284° C.

IR (Nujol) $v cm^{-1}$: 3440, 1715, 1620, 1550, 1260, 1110, 1080, 900.

(4) The above prepared acetaminonaphthoic acid (50.0 g), anhydrous methanol (2000 ml) and conc. sulfuric acid (10 ml) were added, and resulting mixture was refluxed for 1 hour. The reaction mixture was concentrated under reduced pressure, and the residue was poured into a saturated sodium bicarbonate solution, followed by stirring for 1 hour. The precipitated crystals were collected by filtration to give methyl 2-acetamino-1,2,3,4-tetrahydro-5,8-dimethoxy-2-naphthoate. M.P., 160°–162° C.

(5) To a solution of methylsulfinyl carbanion in dimethylsulfoxide prepared from 65% sodium hydride (16 g) and dimethylsulfoxide (200 ml) according to a conventional procedure and cooled at 3° to 10° C., a solution of the above prepared ester (48.0 g) in tetrahydrofuran (500 ml) was dropwise added, and the resulting mixture was stirred at room temperature for 1.5 hours. The reaction mixture was poured into ice water, adjusted to pH 3.5 with conc. hydrochloric acid and extracted with chloroform. The chloroform extract was washed with water, dried over anhydrous magnesium sulfate and concentrated under reduced pressure. The precipitated crystals were collected by filtration to give 2-acetamino-2-(2-methylsulfinyl-1-oxo)ethyl-1,2,3,4-tetrahydro-5,8-dimethoxynaphthalene. M.P., 203°–204° C.

(6)-1 To a solution of the above obtained naphthalene (36.2 g) in tetrahydrofuran (1400 ml) and water (140 ml), amalgamated aluminum prepared from aluminum foil (16 g) and 2% $HgCl_2$ (3000 ml) according to a conventional procedure was added at room temperature. Stirring was continued at room temperature for 30 minutes. Insoluble materials were eliminated by filtration. The filtrate was concentrated under reduced pressure to give 2-acetyl-2-acetamino-1,2,3,4-tetrahydro-5,8-dimethylnaphthalene. M.P., 220°–222° C.

IR (Nujol) $\nu cm^{-1}$: 3260, 1715, 1640, 1550, 1260, 1100, 1085, 790.

(6)-2 A mixture of 2-acetamino-2-(2-methylsulfinyl-1-oxo)ethyl-1,2,3,4-tetrahydro-5,8-dimethoxynaphthalene (7.0 g), zinc powder (5.2 g), benzene (400 ml) and 20% sodium hydroxide solution (70 ml) was refluxed for 6 hours. Insoluble materials were eliminated by filtration. The filtrate was washed with water, dried over anhydrous magnesium sulfate and concentrated under reduced pressure to give 2-acetyl-2-acetamino-1,2,3,4-tetrahydro-5,8-dimethoxynaphthalene. M.P., 218°–220° C.

REFERENCE EXAMPLE 2

(1)-1 A mixture of racemic 2-acetamino-1,2,3,4-tetrahydro-5,8-dimethoxy-2-naphthoic acid (30.1 g), methanol (2500 ml) and l-α-phenylethylamine (12.5 g) was heated under reflux and allowed to stand at room temperature overnight. The precipitated crystals were collected by filtration and recrystallized from methanol (1900 ml) to give the l-α-phenylethylamine salt of l-2-acetamino-1,2,3,4-tetrahydro-5,8-dimethoxy-2-naphthoic acid. (11.8 g). M.P., >280° C. $[\alpha]_D^{20}$ −61.0° (c=0.32, dimethylformamide). This salt (11.7 g) was admixed with 3% hydrochloric acid (800 ml) and stirred at room temperature for 1 hour. The precipitated crystals were collected by filtration to obtain l-2-acetamino-1,2,3,4-tetrahydro-5,8-dimethoxy-2-naphthoic acid (7.7 g). M.P., >280° C. $[\alpha]_D^{20}$ −69.6° (c=1.0, dimethylformamide).

The mother liquors from which the objective compound was separated were combined together and concentrated under reduced pressure. The residue was admixed with 3% hydrochloric acid (1000 ml) and stirred at room temperature for 2 hours. The precipitated crystals were collected by filtration to give 2-acetamino-1,2,3,4-tetrahydro-5,8-dimethoxy-2-naphthoic acid (19.0 g) containing a predominant amount of the d-isomer. The crystals were admixed with methanol (900 ml) and d-α-phenylethylamine (9.0 g), refluxed and allowed to stand at room temperature for 6 hours. The precipitated crystals were collected by filtration and recrystallized from methanol (1500 ml) to give the d-α-phenylethylamine salt of d-2-acetamino-1,2,3,4-tetrahydro-5,8-dimethoxy-2-naphthoic acid (7.8 g). M.P., >280° C. $[\alpha]_D^{20}$ +60.1° (c=0.30, dimethylformamide). This salt (7.5 g) was admixed with 3% hydrochloric acid (500 ml) and stirred at room temperature for 1 hour. The precipitated crystals were collected by filtration to give d-2-acetamino-1,2,3,4-tetrahydro-5,8-dimethoxy-2-naphthoic acid (5.3 g). M.P., >280° C. $[\alpha]_D^{20}$ +68.8° (c=0.98, dimethylformamide).

(1)-2 Racemic 2-acetamino-1,2,3,4-tetrahydro-5,8-dimethoxy-2-naphthoic acid (17.3 g) and l-ephedrine (10 g) were dissolved in methanol (250 ml) while heating and allowed to stand at room temperature 5 hours. The precipitated crystals were collected by filtration and recrystallized from methanol to give the l-ephedrine salt of d-2-acetamino-1,2,3,4-tetrahydro-5,8-dimethoxy-2-naphthoic acid (9.0 g). M.P., 247°–250° C. $[\alpha]_D^{20}$ +37.8° (c=0.5, dimethylformamide). This salt (2.0 g) was admixed with 3% hydrochloric acid (350 ml) and stirred at room temperature for 2 hours. The precipitated crystals were collected by filtration to give d-2-acetamino-1,2,3,4-tetrahydro-5,8-dimethoxy-2-naphthoic acid (1.1 g). M.P., >280° C. $[\alpha]_D^{20}$ +68.9° (c=1.0, dimethylformamide).

(2)-1 A mixture of l-2-acetamino-1,2,3,4-tetrahydro-5,8-dimethoxy-2-naphthoic acid (10.8 g) ($[\alpha]_D^{20}$ −70.2° (c=1.0, dimethylformamide)), anhydrous methanol (430 ml) and conc. sulfuric acid (2 ml) was refluxed for 1.5 hours. After removal of methanol by distillation under reduced pressure, the residue was poured into a saturated sodium bicarbonate solution, and the resulting mixture was stirred at room temperature for 1 hour. The precipitated crystals were collected by filtration to give methyl l-2-acetamino-1,2,3,4-tetrahydro-5,8-dimethoxy-2-naphthoate. M.P., 169°–170° C. $[\alpha]_D^{20}$ −114.5° (c=1.0, chloroform).

(2)-2 In the same manner as in (2)-1 but using d-2-acetamino-1,2,3,4-tetrahydro-5,8-dimethoxy-2-naphthoic acid ($[\alpha]_D^{20}$ +69.4° (c=1.0, dimethylformamide)) (14.5 g), there was prepared methyl d-2-acetamino-1,2,3,4-tetrahydro-5,8-dimethoxy-2-naphthoate. M.P., 169°–170° C. $[\alpha]_D^{20}$ +113.2° (c=1.0, chloroform).

(3)-1 A solution of methyl l-2-acetamino-1,2,3,4-tetrahydro-5,8-dimethoxy-2-naphthoate ($[\alpha]_D^{20}$ −114.5° (c=1.0, chloroform)) (10.2 g) in tetrahydrofuran (120 ml) was dropwise added to a solution of methylsulfinyl carbanion in dimethylsulfoxide prepared from 60% sodium hydride (4 g) and dimethylsulfoxide (50 ml) according to a conventional manner and cooled at 3° to 20° C., and the resulting mixture was stirred at room temperature for 1 hour. The reaction mixture was poured into ice water, adjusted to pH 3.1 with conc. hydrochloric acid and extracted with chloroform. The chloroform layer was washed with water, dried over anhydrous magnesium sulfate and concentrated under reduced pressure. The precipitated crystals were collected by filtration to give l-2-acetamino-2-(2-methylsulfinyl-1-oxo)ethyl-1,2,3,4-tetrahydro-5,8-dimethoxynaphthalene. M.P., 186°–189° C. $[\alpha]_D^{20}$ −65.5° (c=1.0, chloroform).

(3)-2 In the same manner as in (2)-1 but using methyl d-2-acetamino-1,2,3,4-tetrahydro-5,8-dimethoxy-2-naphthoate ($[\alpha]_D^{20}$ +113.2° (c=1.0, chloroform)) (13.0 g), there was prepared d-2-acetamino-2-(2-methylsulfinyl-1-oxo)ethyl-1,2,3,4-tetrahydro-5,8-dimethoxynaphthalene. M.P., 190°–193° C. $[\alpha]_D^{20}$ +66.1° (c=1.1, chloroform).

(4)-1 l-2-Acetamino-2-(2-methylsulfinyl-1-oxo)ethyl-1,2,3,4-tetrahydro-5,8-dimethoxynaphthalene ($[\alpha]_D^{20}$ −65.5° (c=1.0, chloroform)) (9.1 g) was dissolved in a mixture of tetrahydrofuran (500 ml) and water (50 ml), amalgamated aluminum prepared from aluminum foil (7 g) and 2% $HgCl_2$ (1500 ml) by a conventional procedure was added thereto at room temperature, and the resulting mixture was stirred at room temperature for 30 minutes. Insoluble materials were eliminated by filtration. The filtrate was concentrated under reduced pressure to give l-2-acetyl-2-acetamino-1,2,3,4-tetrahydro-5,8-dimethoxynaphthalene. M.P., 227°–228° C. $[\alpha]_D^{20}$ −131.2° (c=1.0, chloroform).

(4)-2 In the same manner as in (4)-1 but using d-2-acetamino-2-(2-methylsulfinyl-1-oxo)ethyl-1,2,3,4-tetrahydro-5,8-dimethoxynaphthalene ($[\alpha]_D^{20}$ +66.1° (c=1.0, chloroform)) (12.0 g), there was prepared d-2-acetyl-2-acetamino-1,2,3,4-tetrahydro-5,8-dimethoxynaphthalene. M.P., 225°–226° C. $[\alpha]_D^{20}$ +134.2° (c=1.0, chloroform).

EXAMPLE 1

2-Acetyl-2-acetamino-1,2,3,4-tetrahydro-5,8-dimethoxynaphthalene (2.8 g), phthalic anhydride (3.4 g), aluminum chloride (40 g) and sodium chloride (8 g) were pulverized and mixed well and charged in a flask previously heated at 180° C. Heating was continued at 180° C. to melt the contents. After melting, heating was further continued for 2 minutes. Then, the temperature was quickly lowered to room temperature, followed by incorporation of a saturated oxalic acid solution (500 ml) cooled with ice water therein. The resultant mixture was stirred at room temperature for 10 minutes. The precipitated crystals were collected by filtration to give 9-acetyl-9-acetamino-6,11-dihydroxy-7,8,9,10-tetrahydro-5,12-naphthacenedione. M.P., 295°–303° C. (decomp.).

IR (Nujol) $\nu cm^{-1}$: 3340, 1710, 1660, 1620, 1590 1530, 1260, 1120, 1040, 970.

EXAMPLE 2

9-Acetyl-9-acetamino-6,11-dihydroxy-7,8,9,10-tetrahydro-5,12-naphthacenedione (8.0 g), anhydrous toluene (1600 ml), ethylene glycol (34 ml) and p-toluenesulfonic acid (1.6 g) were heated and refluxed for 5.5 hours, during which the by-produced water was removed azeotropically. The reaction mixture was decanted to remove tar and concentrated under reduced pressure to make a volume of about 100 ml. The precipitated crystals were collected by filtration to give 9-acetamino-9-(1-ethylenedioxy)ethyl-6,11-dihydroxy-7,8,9,10-tetrahydro-5,12-naphthacenedione. M.P., 273°–275° C.

IR (Nujol) $\nu cm^{-1}$: 3260, 1650, 1610, 1580, 1280, 1250, 1140, 810.

EXAMPLE 3

9-Acetamino-9-(-1-ethylenedioxy)ethyl-6,11-dihydroxy-7,8,9,10-tetrahydro-5,12-naphthacenedione (1.66 g) was dissolved in a mixture of chloroform (50 ml) and carbon tetrachloride (180 ml) while refluxing, and N-bromosuccinimide (1.35 g) was added thereto. The resultant mixture was irradiated with a 500 W visible ray lamp while refluxing for 15 minutes. The reaction mixture was cooled with ice water for 1 hour. The precipitate was collected by filtration, dissolved in chloroform and washed with a saturated sodium bicarbonate solution, 5% sodium thiosulfate and water in order, dried over anhydrous magnesium sulfate and concentrated under reduced pressure. The residue was recrystallized from isopropyl ether to give 9-(1-ethylenedioxy)ethyl-6,11-dihydroxy-7,8,9,10-tetrahydro-7,9-(1-oxa-3-aza-2-methyl-2-propeno)naphthacene-5,12-dione. M.P., 191°–195° C.

IR (Nujol) $\nu cm^{-1}$: 1660, 1640, 1590, 1260, 1220, 1200, 1170, 1040, 970.

EXAMPLE 4

9-Acetyl-9-acetamino-6,11-dihydroxy-7,8,9,10-tetrahydro-5,12-naphthacenedione (200 mg) was dissolved in anhydrous chloroform (200 ml) while refluxing, N-bromosuccinimide (100 mg) was added thereto, and the resultant mixture was heated under reflux while irradiating with a 500 W visible ray lamp over a period of 7 minutes. The reaction mixture was cooled and admixed with a saturated sodium bicarbonate solution. The chloroform layer was separated, washed with 5% thiosulfuric acid and water in order and dried over anhydrous magnesium sulfate. After removal of the solvent by distillation, the residue was purified by chromatography to give 9-acetyl-6,11-dihydroxy- 7,8,9,10-tetrahydro-7,9-(1-oxa-3-aza-2-methyl-2-propeno)naphthacene-5,12-dione. M.P., 200°–204° C.

IR (Nujol) $\nu cm^{-1}$: 1720, 1670, 1620, 1590, 1250, 1210, 1050, 970.

EXAMPLE 5

A mixture of 9-(1-ethylenedioxy)ethyl-6,11-dihydroxy-7,8,9,10-tetrahydro-7,9-(1-oxa-3-aza-2-methyl-2-propeno)naphthacene-5,12-dione (1.24 g), dioxane (24 ml), water (24 ml) and conc. hydrochloric acid (6 ml) was heated under reflux for 13 hours. After removal of the solvent by distillation under reduced pressure, the residue was dissolved in methanol (30 ml), activated charcoal (200 mg) was added thereto, and the resultant mixture was stirred. Insoluble materials were eliminated by filtration. The filtrate was concentrated under reduced pressure. The residue was recrystallized from isopropanol to give 9-amino-9-acetyl-6,7,11-trihydroxy-7,8,9,10-tetrahydro-5,12-naphthacenedione hydrochloride. M.P., 218°–223° C.

IR (Nujol) $\nu cm^{-1}$: 3400, 1720, 1620, 1590, 1260, 1160, 1120, 990.

EXAMPLE 6

A mixture of 9-acetyl-6,11-dihydroxy-7,8,9,10-tetrahydro-7,9-(1-oxa-3-aza-2-methyl-2-propeno)naphthacene-5,12-dione (61 mg), water (4 ml) and conc. hydrochloric acid (1 ml) was heated at a temperature of 90° to 100° C. for 3 hours. The reaction mixture was concentrated under reduced pressure to give 9-amino-9-acetyl-6,7,11-trihydroxy- 7,8,9,10-tetrahydro-5,12-naphthacenedione hydrochloride. M.P., 210°–215° C.

IR (Nujol) $\nu cm^{-1}$: 3400, 1720, 1620, 1590, 1260, 1160, 1120, 990.

EXAMPLE 7

A mixture of 9-amino-9-acetyl-6,7,11-trihydroxy-7,8,9,10-tetrahydro-5,12-naphthacenedione hydrochloride (130 mg), sodium carbonate (400 mg), a saturated sodium bicarbonate solution (20 ml), chloroform (10 ml) and tetrahydrofuran (10 ml) was stirred vigorously, and acetyl chloride (200 mg) was dropwise added thereto at room temperature. After the dropwise addition was completed, stirring was continued for 30 minutes. The reaction mixture was shaken with chloroform (50 ml). The chloroform layer was separated, washed with water, dried over anhydrous magnesium sulfate and concentrated. The residue was recrystallized from diethyl ether to give 9-acetyl-9-acetamino-6,7,11-trihydroxy-7,8,9,10-tetrahydro-5,12-naphthacenedione. M.P., 240°–248° C.

IR (Nujol) $\nu cm^{-1}$: 3300, 1710, 1650, 1620, 1590, 1250, 1030, 980.

EXAMPLE 8

To a solution of 9-amino-9-acetyl-6,7,11-trihydroxy-7,8,9,10-tetrahydro-5,12-naphthacenedione hydrochloride (130 mg) in a mixture of methylene chloride (10 ml) and pyridine (1 ml), trifluoroacetic anhydride (300 mg) was dropwise added thereto at room temperature while stirring. After the dropwise addition was completed, stirring was continued for 1 hour. The reaction mixture was poured into 3% hydrochloric acid and extracted with chloroform. The chloroform extract was washed with water, a saturated sodium bicarbonate solution and water in order, dried over anhydrous magnesium sulfate and concentrated under reduced pressure. The residue was purified by chromatography to give 9-acetyl-9-trifluoroacetamino-6,7,11-trihydroxy-7,8,9,10-tetrahydro-5,12-naphthacenedione. M.P., 218°–221° C.

IR (Nujol) $\nu$cm$^{-1}$: 3300, 1710, 1620, 1590, 1260, 1200, 1140.

EXAMPLE 9

To a mixture of 9-amino-9-acetyl-6,7,11-trihydroxy-7,8,9,10-tetrahydro-5,12-naphthacenedione hydrochloride (550 mg) and anhydrous pyridine (10 ml), acetic anhydride (3 ml) was added thereto while cooling with ice water. The resultant mixture was heated at a temperature of 60° to 65° C. for 30 minutes. The reaction mixture was poured into 3% hydrochloric acid and extracted with chloroform. The chloroform extract was washed with water, a saturated sodium bicarbonate solution and water in order, dried over anhydrous magnesium sulfate and concentrated under reduced pressure. The residue was purified by chromatography to give 9-acetyl-9-acetamino-6,7,11-triacetoxy-7,8,9,10-tetrahydro-5,12-naphthacenedione. M.P., 276°–278° C.

IR (Nujol) $\nu$cm$^{-1}$: 3450, 1770, 1740, 1720, 1680, 1590, 1260, 1230, 1190, 1020.

EXAMPLE 10

A mixture of 9-acetyl-9-acetamino-6,11-dihydroxy-7,8,9,10-tetrahydro-5,12-naphthacenedione (3.0 g), acetic acid (90 ml) and conc. hydrochloric acid (60 ml) was heated under reflux for 9 hours. The reaction mixture was concentrated under reduced pressure. The residue was admixed with a saturated sodium bicarbonate solution (1000 ml), followed by stirring for 1 hour. The precipitated crystals were collected by filtration to give 9-acetyl-9-amino-6,11-dihydroxy-7,8,9,10-tetrahydro-5,12-naphthacenedione (2.6 g). M.P., 190°–195° C.

IR (Nujol) $\nu$cm$^{-1}$: 3350, 1705, 1615, 1580, 1250, 1120, 970, 790.

EXAMPLE 11

To a solution of 9-acetyl-9-amino-6,11-dihydroxy-7,8,9,10-tetrahydro-5,12-naphthacenedione (1.34 g) in anhydrous methylene chloride (30 ml), trifluoroacetic anhydride (4.0 g) was dropwise added thereto while cooling with ice water. Stirring was continued for 3.5 hours. The precipitated crystals were collected by filtration to give 9-acetyl-9-trifluoroacetylamino-6,11-dihydroxy-7,8,9,10-tetrahydro-5,12-naphthacenedione (1.6 g). M.P., 252°–256° C.

IR (Nujol) $\nu$cm$^{-1}$: 3290, 1740, 1700, 1620, 1585, 1560, 1260, 1200, 1160, 1040.

EXAMPLE 12

A mixture of 9-acetyl-9-trifluoroacetamino-6,11-dihydroxy-7,8,9,10-tetrahydro-5,12-naphthacenedione (1.3 g), toluene (250 ml), p-toluenesulfonic acid (0.29 g) and ethylene glycol (4 ml) was heated under reflux for 10 hours, during which the by-produced water was eliminated azeotropically. The reaction mixture was poured into a saturated sodium bicarbonate solution. The toluene layer was separated, washed with water, dried over anhydrous magnesium sulfate and concentrated under reduced pressure to make a residual amount of about 10 grams. The precipitates were collected by filtration to give 9-trifluoroacetamino-9-(1-ethylenedioxy)ethyl-6,11-dihydroxy-7,8,9,10-tetrahydro-5,12-naphthacenedione (1.2 g). M.P., 228°–230° C.

IR (Nujol) $\nu$cm$^{-1}$: 3320, 1725, 1620, 1580, 1550, 1250, 1185, 1035, 780.

EXAMPLE 13

9-Trifluoroacetamino-9-(1-ethylenedioxy)ethyl-6,11-dihydroxy-7,8,9,10-tetrahydro-5,12-naphthacenedione (200 mg) was dissolved in a mixture of chloroform (9 ml) and carbon tetrachloride (30 ml), N-bromosuccinimide (170 mg) was added thereto, and the resultant mixture was refluxed for 15 minutes while irradiating with a 500 W visible ray lamp. The reaction mixture was cooled with ice water, and chloroform (50 ml) was added thereto. The chloroform layer was washed with a saturated sodium bicarbonate solution, 5% sodium thiosulfate and water in order, dried over anhydrous magnesium sulfate and concentrated under reduced pressure to give 9-(1-ethylenedioxy)ethyl-6,11-dihydroxy-7,8,9,10-tetrahydro-7,9-(1-oxa-3-aza-2-trifluoromethyl-2-propeno)naphthacene-5,12-dione. M.P., 196°–199° C.

IR (Nujol) $\nu$cm$^{-1}$: 1700, 1630, 1590, 1260, 1210, 1150, 1040, 980.

EXAMPLE 14

A mixture of 9-(1-ethylenedioxy)ethyl-6,11-dihydroxy-7,8,9,10-tetrahydro-7,9-(1-oxa-3-aza-2-trifluoromethyl-2-propeno)naphthacene-5,12-dione (60 mg), dioxane (4 ml), water (4 ml) and conc. hydrochloric acid (1 ml) was refluxed for 5 hours. The reaction mixture was concentrated under reduced pressure, and the residue was recrystallized from isopropanol to give 9-amino-9-acetyl-6,7,11-trihydroxy-7,8,9,10-tetrahydro-5,12-naphthacenedione hydrochloride. M.P., 223°–228° C.

IR (Nujol) $\nu$cm$^{-1}$: 3400, 1720, 1620, 1590, 1260, 1160, 1120, 990.

EXAMPLE 15 l-2-Acetyl-2-acetamino-1,2,3,4-tetrahydro-5,8-dimethoxynaphthalene (2.8 g) ($[\alpha]_D^{20}$ −131.2° (c=1.0, chloroform)), phthalic anhydride (3.4 g), aluminum chloride (40 g) and sodium chloride (8 g) were pulverized and mixed well. The resultant mixture was charged in a flask previously heated at 180° C., and heating was continued at 180° C. to melt the contents. After melting, heating was further continued 2 minutes. The reaction mixture was cooled quickly to room temperature and added to a saturated oxalic acid solution (500 ml) cooled with ice water. Stirring was effected at room temperature for 10 minutes. The precipitated crystals were collected by filtration to give l-9-acetyl-9-acetamino-6,11-dihydroxy-7,8,9,10-tetrahydro-5,12-naphthacenedione. M.P., 300° C. $[\alpha]_D^{20}$ −85° (c=0.05, dimethylformamide).

IR (Nujol) $\nu$cm$^{-1}$: 3340, 1705, 1670, 1620, 1585, 1520, 1250, 1110, 1040, 970.

EXAMPLE 16

A mixture of l-9-acetyl-9-acetamino-6,11-dihydroxy-7,8,9,10-tetrahydro-5,12-naphthacenedione (6.39 g), anhydrous toluene (1400 ml), ethylene glycol (23 ml) and p-toluenesulfonic acid (1.1 g) was refluxed for 5.5 hours, during which the by-produced water was eliminated azeotropically. The reaction mixture was poured into a saturated sodium bicarbonate solution (1000 ml). The toluene layer was separated, washed with water, dried over anhydrous magnesium sulfate and concentrated under reduced pressure to make a volume of about 100 ml. The precipitated crystals were collected by filtration to give 1-9-acetamino-9-(1-ethylenedioxy)ethyl-6,11-dihydroxy-7,8,9,10-tetrahydro-5,12-naphthacenedione. M.P., 259°-262° C. (decomp.). $[\alpha]_D^{20}$ −308° (c=0.23, chloroform).

IR (Nujol) $\nu$cm$^{-1}$: 3260, 1660, 1610, 1580, 1280, 1250, 1200, 1140, 810, 790.

EXAMPLE 17

1-9-Acetamino-9-(1-ethylenedioxy)ethyl-6,11-dihydroxy-7,8,9,10-tetrahydro-5,12-naphthacenedione (5.56 g) was dissolved in a mixture of chloroform (160 ml) and carbon tetrachloride (700 ml) while refluxing, and N-bromosuccinimide (4.53 g) was added thereto. The resultant mixture was refluxed for 20 minutes while irradiating with a 500 W visible ray lamp. The reaction mixture was cooled with ice water for 1 hour. The precipitate was collected by filtration, dissolved in chloroform, washed with a saturated sodium bicarbonate solution, 5% sodium thiosulfate and water in order, dried over anhydrous magnesium sulfate and concentrated under reduced pressure. The residue was recrystallized from isopropyl ether to give d-9-(1-ethylenedioxy)ethyl-6,11-dihydroxy-7,8,9,10-tetrahydro-7,9-(1-oxa-3-aza-2-methyl-2-propeno)naphthacene-5,12-dione. M.P., 160°-165° C. $[\alpha]_D^{20}$ +376.3° (c=0.22, chloroform).

IR (Nujol) $\nu$cm$^{-1}$: 1660, 1620, 1580, 1270, 1230, 1200, 1100, 1030, 970.

EXAMPLE 18

A mixture of d-9-(1-ethylenedioxy)ethyl-6,11-dihydroxy-7,8,9,10-tetrahydro-7,9-(1-oxa-3-aza-2-methyl-2-propeno)naphthacene-5,12-dione (4.35 g), dioxane (70 ml), water (70 ml) and conc. hydrochloric acid (18 ml) was refluxed for 15 hours. After removal of the solvent by distillation under reduced pressure, the residue was dissolved in methanol (400 ml), activated charcoal (350 mg) was added thereto, and the resultant mixture was stirred. Insoluble materials were eliminated by filtration. The filtrate was concentrated under reduced pressure, and the residue was recrystallized from isopropanol to give 1-9-amino-9-acetyl-6,7,11-trihydroxy-7,8,9,10-tetrahydro-5,12-naphthacenedione hydrochloride. M.P., 224°-230° C. $[\alpha]_D^{20}$ −89° (c=0.1, dimethylformamide).

IR (Nujol) $\nu$cm$^{-1}$: 3400, 1720, 1620, 1590, 1260, 1240, 1160, 1130, 1000, 970.

EXAMPLE 19

1-9-Amino-9-acetyl-6,7,11-trihydroxy-7,8,9,10-tetrahydro-5,12-naphthacenedione hydrochloride (130 mg) was dissolved in a mixture of methylene chloride (10 ml) and pyridine (1 ml), and trifluoroacetic anhydride (300 mg) was dropwise added thereto at room temperature while stirring. After the dropwise addition was completed, stirring was further continued for 1 hour. The reaction mixture was poured into 3% hydrochloric acid and extracted with chloroform. The chloroform extract was washed with water, a saturated sodium bicarbonate solution and water in order, dried over anhydrous magnesium sulfate and concentrated under reduced pressure. The residue was purified by chromatography to give d-9-acetyl-9-trifluoroacetamino-6,7,11-trihydroxy-7,8,9,10-tetrahydro-5,12-naphthacenedione. M.P., 236°-238° C. $[\alpha]_D^{20}$ +207° (c=0.2, chloroform).

IR (Nujol) $\nu$cm$^{-1}$: 3500, 3300, 1720, 1620, 1590, 1540, 1240, 1210, 1160, 990.

What is claimed is:
1. A compound of the formula:

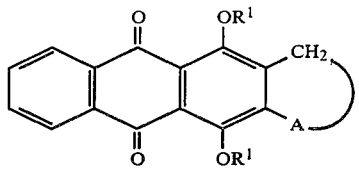

wherein A is the group:

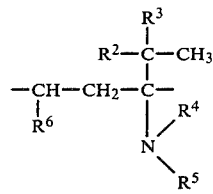

wherein $R^1$ is a hydrogen atom or a group of the formula: $-COR^7$, $R^2$ and $R^3$ are each a lower alkoxy group or, when taken together, represent an ethylenedioxy group or an oxo group, $R^4$ and $R^5$ are both hydrogen atoms or either one of them is a hydrogen atom and the other is a group of the formula: $-COR^7$, $R^6$ is a hydrogen atom, a hydroxyl group or a group of the formula: $-OCOR^7$ and $R^7$ is a lower alkyl group, a halo(lower)alkyl group, a phenyl group or a halophenyl group.

2. The compound according to claim 1 wherein $R^1$ is hydrogen.

3. The compound according to claim 2 or 1, wherein $R^6$ is hydroxyl.

4. The compound according to claims 2 or 1, wherein $R^2$ and $R^3$ represent oxo.

5. A compound of the formula:

wherein A is a group of the formula:

$R^1$ is hydrogen, $R^2$ and $R^3$ represent oxo, $R^4$ is hydrogen, $R^5$ is hydrogen or $\phi COR^7$ where $R^7$ is a lower alkyl group, a halo (lower) alkyl group, a phenyl group or a halophenyl group and $R^6$ is hydroxyl.

6. The compound according to claim 5, wherein $R^5$ is hydrogen.

7. An anti-tumor or anti-microbial composition which comprises an effective anti-tumor amount or effective anti-microbial amount of a compound of claim 1 as an active ingredient and a pharmaceutically acceptable carrier or diluent.

* * * * *